United States Patent [19]

Sivam

[11] Patent Number: 4,981,979

[45] Date of Patent: Jan. 1, 1991

[54] IMMUNOCONJUGATES JOINED BY THIOETHER BONDS HAVING REDUCED TOXICITY AND IMPROVED SELECTIVITY

[75] Inventor: Gowsala Sivam, Edmonds, Wash.

[73] Assignee: NeoRx Corporation, Wash.

[21] Appl. No.: 95,178

[22] Filed: Sep. 10, 1987

[51] Int. Cl.$^5$ ............... C07D 207/40; G01N 33/536; C07K 1/00

[52] U.S. Cl. ............................... 548/545; 436/544; 436/547; 530/389; 530/390; 530/391; 530/403; 530/404; 530/405; 548/546; 548/547

[58] Field of Search ............... 435/7; 436/544, 545, 436/546, 547, 501; 530/389, 340, 391, 402, 403, 404, 405; 548/545, 546, 547

[56] References Cited

U.S. PATENT DOCUMENTS 4,429,008  1/1984  Martin et al. .................. 436/501
4,434,236  2/1984  Freytag ........................ 436/512

(List continued on next page.)

FOREIGN PATENT DOCUMENTS 1203164  4/1986  Canada.

OTHER PUBLICATIONS

Y. Masuho et al., *Biochem. Biophys. Res. Comm.* 102:561 (1981).

(List continued on next page.)

*Primary Examiner*—Estler M. Kepplinger
*Assistant Examiner*—Florina B. Hoffer
*Attorney, Agent, or Firm*—Debra K. Leith

[57] ABSTRACT

Method for producing an immunoconjugate comprising the steps of reacting a toxin or protein with a heterobifunctional reagent having the following general formula:

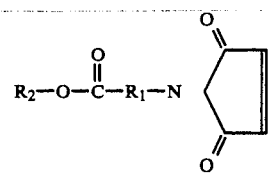

where $R_1$ is:

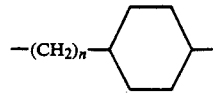

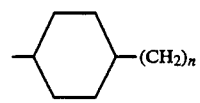

where n=1 to 10; and where $R_2$ is selected from the group consisting of o- and p-nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, 2-fluorophenyl, 4-fluorpheyl, 2,4-difluorophenyl, o-nitro-p-sulfophenyl, N-hydroxyphthalimide, N,N-diethylamino, N-hydroxypyrrolidone, tetrafluorothiophenyl, and 2,3,5,6-tetrafluorophenyl, under reactive conditions, thereby forming a derivatized toxin or protein. The derivatized toxin or protein is separated from the reaction mixture and combined with an antibody or antibody fragment under reactive conditions, such that at least one native disulfide bond is reduced to produce at least one thiol group, capable of forming a thioether bond between said thiol group and the maleimide group of said derivatized toxin, or protein thereby forming an immunoconjugate. The preferred heterobifunctional linking group is succinimidyl 4-(N-maleimidomethyl)-cyclohexane-1-carboxylate (SMCC).

8 Claims, 6 Drawing Sheets

U.S. PATENT DOCUMENTS

| | | | |
|---|---|---|---|
| 4,507,234 | 3/1985 | Kato et al. | 260/121 |
| 4,520,226 | 5/1985 | Neville, Jr. et al. | 424/85 |
| 4,545,985 | 10/1985 | Pastan et al. | 424/85 |
| 4,618,492 | 10/1986 | Blattler et al. | 424/85 |
| 4,643,895 | 2/1987 | Casellas et al. | 424/85 |
| 4,657,853 | 4/1987 | Freytag et al. | 435/7 |
| 4,659,839 | 4/1987 | Nicolotti et al. | 548/546 |
| 4,678,667 | 7/1987 | Meares et al. | 424/85 |
| 4,680,338 | 7/1987 | Sundoro | 525/54.1 |
| 4,816,390 | 3/1989 | Kondo et al. | 436/518 |

OTHER PUBLICATIONS

J. Marsh and D. Neville, *Biochem.* 25:4461 (1986).

S. Ramakrishnan and L. Houston, *Cancer Res.* 44:201 (1984).

Y. Masuho et al., *J. Biochem.* 91:1583 (1982).

J. Lambert et al., *J. Biol. Chem.* 260:12035 (1985).

M. Bjorn et al., *Cancer Res.* 46:3262 (1986).

L. Barbieri and F. Stirpe, *Canc. Surv.* 1:489 (1982).

*Pierce Chemical Co. Catalog* (1983).

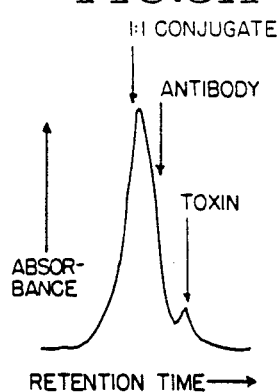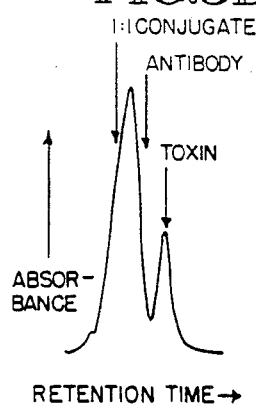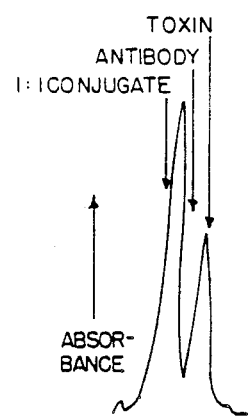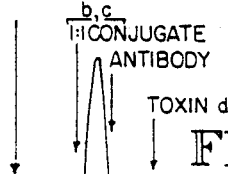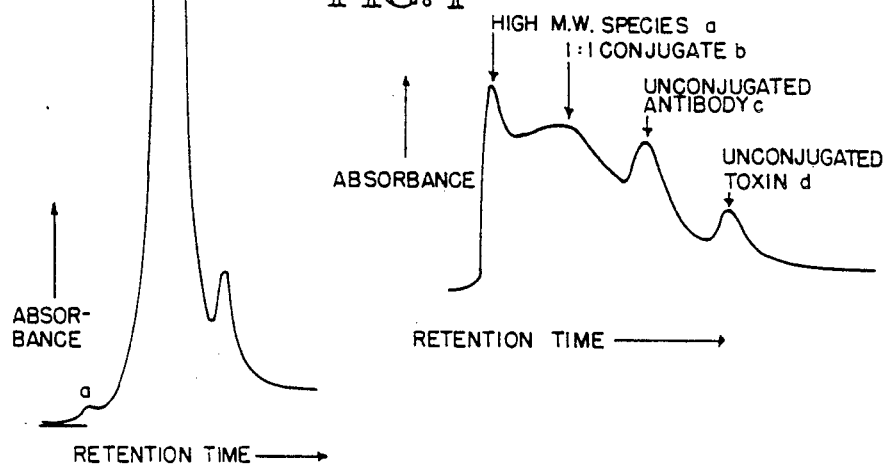

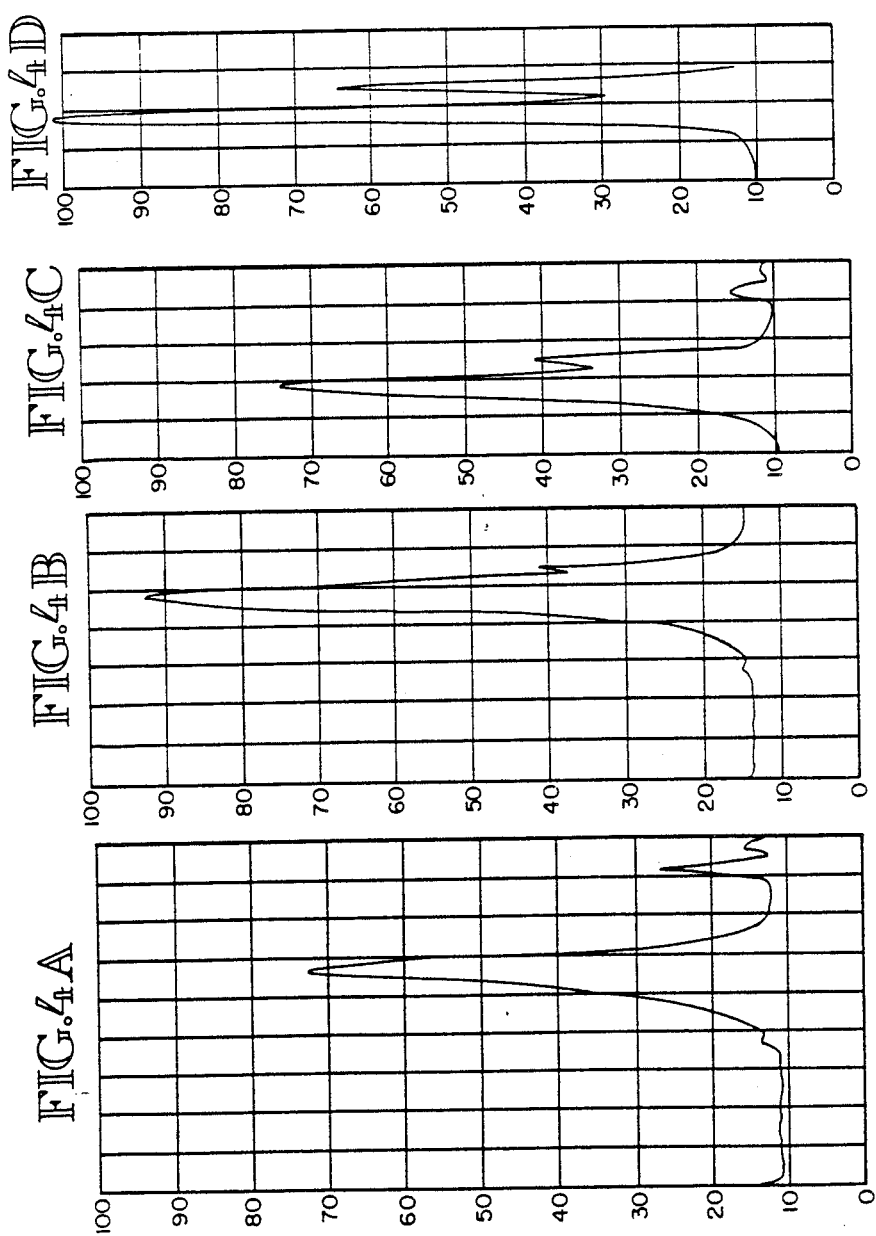

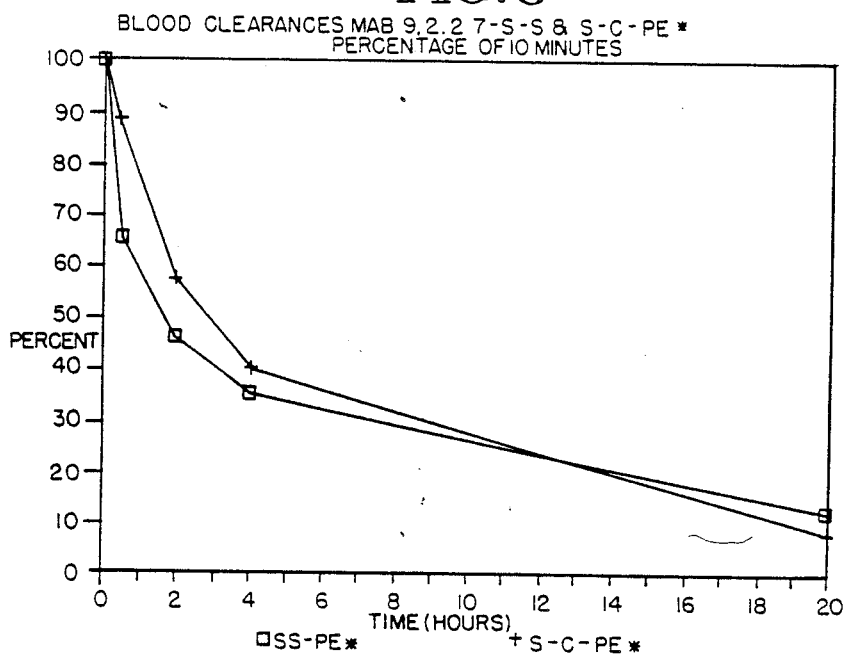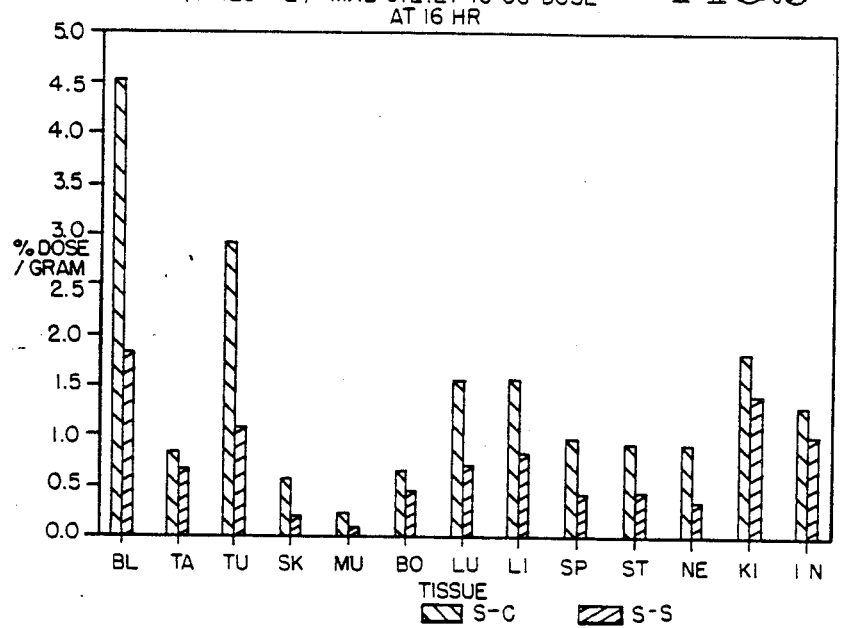

IMMUNOCONJUGATES JOINED BY THIOETHER BONDS HAVING REDUCED TOXICITY AND IMPROVED SELECTIVITY

TECHNICAL FIELD

The present invention relates generally to improved immunoconjugates that offer increased selectivity for target cells with reduced toxicity for the recipient, and methods for making and using these improved immunoconjugates.

BACKGROUND ART

Immunoconjugates are covalently bonded hybrid molecules composed of a recognition portion, such as an antibody molecule, an antibody fragment, or a functional equivalent thereof, and a biologically active portion, such as a toxin, a toxin fragment, a drug, a biologic response modifier, or a radioisotope. Immunoconjugates have enormous potential as potent anti-tumor agents, due to the selectivity imparted to the hybrid molecules by the antibody portion of the immunoconjugate. The exquisite selectivity of antibodies or antibody fragments permits delivery of increased doses of cytotoxic, inhibitory or radiolabeled moieties to a defined population of cells.

Originally, immunoconjugates were formed using polyclonal antibodies coupled to toxin molecules. Recently, the development of hybridoma technology has made available monoclonal antibodies that bind to a specific epitope of an antigen. This is in contrast to polyclonal antibodies that bind to multiple antigens or epitopes. Although monoclonal antibodies or fragments thereof offer improved specificity and reproducibility of a given hybrid molecule, certain technical problems in the preparation of immunoconjugates have been recognized.

For example, the linkage of antibody to toxin is one variable that has been examined by several investigators. In general, immunoconjugates may be formed by linking two molecules through disulfide bonds, which can be reductively cleaved, or by linking through bonds that are not affected by reducing agents, such as amide or thioether bonds.

Intact toxin molecules, such as diphtheria toxin, ricin, and abrin, are composed of an A chain and a B chain linked by a disulfide bond. The B chain of ricin binds to specific receptors on the surface of target cells, and is believed to participate in the internalization of the A chain. The A chain contains the biologically active portion of the toxin molecule. Upon reduction of the disulfide bond between the A and B chains, the A chain is released into the cytoplasm and participates in a biochemical reaction that results in inhibition of protein synthesis in target cells. Therefore, it might be expected that immunoconjugates of A chains would require a cleavable bond between antibody and hemitoxin to exhibit cytotoxicity.

Disulfide-bonded immunoconjugates were initially believed to be necessary to mimic the disulfide linkage of A and B chains of native toxin. This native disulfide bond had to be reductively cleaved to liberate the active A chain of the toxin molecule within the cell.

Linkage of A chains of toxins with antibodies through non-reducible bonds generally produced immunoconjugates of decreased potency. For instance, one early study reported that conjugates of polyclonal antibody and the A chain of diphtheria toxin, joined by a linker that did not contain a reducible bond, were one-third as active against target cells as conjugates linked with disulfide bond (Y. Masuho et al., *Biochem. Biophys. Res. Comm.* 102:561, 1981). This result was not surprising as optimum activity of diphtheria toxin requires limited proteolysis to allow reduction and release of the enzymatic portion.

Masuho et al. subsequently examined four ricin A chain immunoconjugates joined with different linkages (Y. Masuho et al., *J. Biochem.* 91:1583, 1982). Monovalent Fab'-SH fragments of polyclonal antibodies were cross-linked to A chain using 5,5'-dithio bis (2-nitrobenzoic aoid) to form disulfide bonds or N, N'-o-phenylenedimaleimide (PDM) to form thioether bonds. Reaction with PDM yielded essentially pure heterodimer (Fab'-PDM-A chain) without formation of the homodimer (Fab'-PDM-Fab'). Divalent F(ab')$_2$ fragments of the same polyclonal antibody were substituted with N-succinimidyl 3-(2-pyridyldithio) propionate (SPDP) or N-succinimidyl m-(N-maleimido) benzoate (SMB) prior to mixing with ricin A chain. In these reactions, the coupling reagents react with lysine residues of the F(ab')$_2$ fragment to form an amide bond; the sulfhydryl group of the A chain reacts with the activated disulfide bond of SPDP to form a disulfide bond between A chain and antibody or with the maleimide group of SMB to form a thioether bond. The PDM and SMB conjugates were resistant to cleavage with 2-mercaptoethanol (2-ME). Upon examination of the reaction products, the F(ab')$_2$ immunoconjugates were found to be substituted with 0, 1, 2, or 3 molecules of ricin A chain, with a 1:1 ratio of F(ab')$_2$:ricin A chain predominant.

Upon comparison, immunotoxins of polyclonal antibodies or antibody fragments conjugated to ricin A chain were 54–80 times more toxic when linked by a cleavable disulfide bond, rather than a noncleavable thioether or amide bond. The reduction in activity was not due to a blocking effect of the antibody or Fab' fragment on the enzymatic activity of the A chain, further suggesting that the A chain must be liberated from the cell binding moiety to exhibit cytotoxicity.

Masuho et al. also investigated the effects of antigen-binding valency on cytotoxic activity, and reported that divalent binding as with intact antibody or F(ab')$_2$, was superior to monovalent (Fab') binding. Since F(ab')$_2$ and Fab' fragments do not have an Fc region, which mediates non-antigen specific binding to cells, specificity of immunoconjugates should be improved in vivo.

Other investigators have examined the effects of cleavable and noncleavable linkers on the toxicity of A chain- and hemitoxin-containing conjugates (S. Ramakrishnan and L. Houston, *Canc. Res.* 44:201, 1984). Hemitoxins possess an enzyme activity functionally equivalent to that of A chain, but do not have an associated delivery polypeptide analogous to B chain. Pokeweed antiviral protein (PAP), a hemitoxin, does not contain native free thiol groups, and thus thiol groups need be introduced by reaction with an agent such as SPDP, followed by reduction. Reduction produces free sulfhydryl groups, with the average number of 1.24 per PAP molecule. Monoclonal antibodies (MAbs) directed against Thy 1.1 were subsequently derivatized with SPDP and conjugated with SPDP-PAP overnight in the cold using a 3-fold molar excess of PAP over IgG. The resulting immunoconjugate contained a cleavable disulfide bond.

Alternatively, a noncleavable immunoconjugate was formed by first reacting MAb with m-maleimidobenzoyl-N-hydroxysuccinimide ester (MBS), and then reacting the MAb-MBS protein with reduced SPDP-PAP. The formation of thioether bonds was performed at 4° C overnight. Similar conjugates were formed with ricin A chain.

All immunoconjugates were highly specific for Thy 1.1-positive cells, however, variations in cytotoxicity were observed when different Thy 1.1 MAbs were incorporated into immunoconjugates. Ricin immunoconjugates (MAb 31-E6 and ricin A chain) joined by a noncleavable linker were effective inhibitors of in vitro translation, but were ineffective inhibitors of protein synthesis when incubated with intact target cells.

Unlike ricin A chain conjugates, PAP immunoconjugates (MAb 31-E6 and PAP) were as active with cleavable or non-cleavable linkers. These data indicated that PAP immunoconjugates do not require cleavage of the toxic moiety for inhibitory activity.

The observations of Ramakrishnan and Houston could not be confirmed in a subsequent study (J. Lambert et al., *J. Biol. Chem.* 260:12035, 1985). These investigators found that a cleavable linkage was required for cytotoxic activity of gelonin and PAP immunoconjugates, consistent with previous findings reported in the literature regarding the necessity of cleavage of A chain conjugates.

Recently, PE and ricin A chain immunoconjugates, linked with disulfide or thioether bonds, were assayed for human breast cancer cytotoxicity in vitro (M. Bjorn et al., *Canc. Res.* 46:3262, 1986). For preparation of disulfide-linked conjugates, PE was derivatized with 2-iminothiolane (IT). MAbs derivatized with SPDP were then reacted with PE-IT for 15-20 hours at 4° C. to yield disulfide-bonded conjugates. Thioether-linked conjugates were formed by reacting MAbs with the maleimido-6-aminocaproyl ester of 4-hydroxy-3-nitrobenzene sulfonic acid prior to mixing with PE-IT in a 1:3 (MAb:PE) molar ratio for 15-20 hours at 4° C. The resultant immunoconjugates were predominantly 1:2 (Ab to PE or ricin A chain).

The cytotoxicities of an analogous disulfide-linked and thioether-linked MAb-PE immunoconjugate were compared. The cleavable and noncleavable PE immunoconjugates displayed similar cytotoxic activities against two different target cells. In contrast, thioether-linked ricin A chain conjugates were less cytotoxic in vitro than the analogous disulfide-linked conjugates. The in vivo relevancy of these findings was unclear, since comparative in vivo studies were not performed. In a separate study, in vivo plasma clearance and stability of MAb-PE immunoconjugates in mice have been reported to be essentially the same for disulfide and thioether-linked immunoconjugates (L. Barbieri and F. Stirpe, *Canc. Surv.* 1:489, 1982).

Immunoconjugates of *Pseudomonas* exotoxin (PE) coupled to MAbs or to EGF through either disulfide or thioether linkages were disclosed in a recent patent (I. Pastan et al., U.S. Pat. No. 4,545,985, 1985). PE was treated with methyl-4-mercaptobutyrimidate (MMB), so as to introduce two thiol groups per PE molecule. MMB-PE was then reacted with dithiobis(2-nitrobenzoic acid) (DTNB), forming a PE derivative possessing disulfide bonds. MMB-derivatized MAb, which contains slightly more than 1 thiol group per MAb molecule, was then reacted with a 3-fold molar excess of DTNB-activated MMB-PE at room temperature for 2 hours. The conjugation of MMB-PE to MMB-EGF was performed in the presence of an excess of derivatized PE, and the reaction was allowed to go to completion. The patent postulated that MBS-modified MAb could be reacted with MMB-PE to yield a putative thioether-linked immunoconjugate. However, the production of MAb-PE immunoconjugates linked by thioether bonds was neither reduced to practice nor claimed. The reactants in this mixture could also yield disulfide-bonded PE-MMB-MAb, through reaction of MMB-PE with native disulfide bonds of MAb. Data comparing thioether- and disulfide-linked conjugates were not reported by Pastan et al.

The ratio of toxin:antibody present in immunoconjugates may also affect the specificity and cytotoxicity of the hybrid molecules. One report suggested that the cytotoxicity of holotoxin-immunoconjugates may be potentiated when immunoglobulin:ricin was in a ratio of 1:2, rather than 1:1. (J. Marsh and D. Neville, Jr., *Biochem.* 25:4461, 1986). Whole MAb thiolated with 2-iminothiolane and MBS-substituted ricin were combined in a 10:1 molar ratio of ricin:MAb. The yield of 1:1 species of immunoconjugates was reported to be in the range of 3%-8%. The authors compared conjugation with DTT-reduced MAb, which resulted in 10 -SH groups/antibody and concluded that it was desirable to introduce a limited number of thiol groups via heterobifunctional reagents into MAbs rather than using native sulfhydryl groups.

The literature reflects the historical development of approaches to immunoconjugate syntheses. Preliminary studies of the efficacy of "magic bullets" used reduced polyclonal antibodies linked to reduced toxins to form immunoconjugates. This method of conjugation was relatively uncontrolled and unpredictable, since antibody and ricin disulfide bonds could reform as readily as antibody-toxin hybrids. Heterobifunctional reagents became preferred compounds for linking antibody to toxin, because the amount of free sulfhydryl groups available for subsequent conjugation, and thus ratios of antibody to toxin in the immunoconjugate product, could be controlled. The presence of two different reactive end groups on heterobifunctional reagents permitted directed, predictable, and reproducible reaction of the linking agents.

A variety of reagents have been used in the literature to derivatize antibody or toxin molecules. However, most recently reported methods of producing immunoconjugates join derivatized toxin to derivatized antibody. U.S. Pat. No. 4,520,226 discloses MAb for immunotoxin production derivatized with MBS, but yields and in vivo utility were not reported. Most synthetic protocols generally combine antibody with a 3- to 10-fold molar excess of derivatized toxin. Thus, preparation of derivatized toxin represents a significant effort of labor and expense. Also removal of unreacted toxin presents a significant manufacturing problem.

Further, the conditions described in the art for conjugation of antibody and toxin often involve long reaction times. In addition, even with the relatively controlled conditions of conjugation presently used, the immunoconjugate products are often heterogeneous, and must be purified from unreacted components and undesired species, thereby significantly reducing the yield of the desired end product to thirty percent or less.

There are little data supporting the in vivo efficacy of immunoconjugate therapy. Most in vivo treatment has been disappointing due to (1) nonspecific toxicity of the immunoconjugates, which limits the amount of conjugate that can be administered; and (2) reduced delivery of toxin to the target site as a result of premature cleavage of the disulfide linkage in vivo, or binding to receptors in normal tissues, e.g., liver. In the latter case, premature release of toxins, especially holotoxins, can greatly increase nonspecific toxicity. Cocktails of immunotoxins have been explored for increasing efficacy of treatment ex vivo. Donor bone marrow cells were treated ex vivo with immunoconjugates cytotoxic for T-cells, prior to infusion into patients, for treatment of GVHD (D. Neville, Jr. and R. Youle, U.S. Pat. No. 4,520,226, 1985). The combination of three different anti T-cell conjugates improved T-cell depletion compared to single antibodies. This procedure has not yet been tested for in vivo application.

As a result of the above-noted disadvantages of current immunoconjugates, there is a need in the art for improved immunoconjugates that can be efficiently and rapidly synthesized in high yield and that exhibit reduced nonspecific toxicity in vivo. Conjugates possessing these properties will permit administration of an effective in vivo therapeutic dose of an immunoconjugate that is delivered efficiently to targeted tumor sites. The method of conjugation should conserve toxin by minimizing the ratio of toxin offered to antibody. Finally, such conjugates should be linked through a more stable thioether bond, rather than less stable disulfide bonds, using native sulfhydryl groups in the antibody or toxin. The present invention fulfills these needs, and further provides other related advantages.

DISCLOSURE OF THE INVENTION

The present invention provides an efficient (e.g., >50% yield) method for producing immunoconjugates having a desired ratio of protein to antibody of approximately 1:1, while offering a minimal (e.g., 1:1) molar ratio of protein to antibody. Moreover, the conjugates produced by the method of the present invention are linked through a thioether bond that provides efficient conjugation, resulting in high yields and reduced times of conjugation. The linkage reaction is preferably conducted with an optimal pH and concentration of reducing agent to generate a minimum of one sulfhydryl group (derived from a native disulfide bridge) and one maleimido group on antibody and protein, respectively.

The invention provides a method of producing immunoconjugates comprising the steps of reacting a protein with a heterobifunctional reagent having the following general formula:

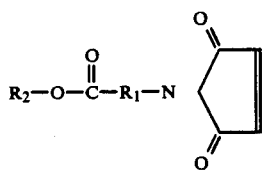

where $R_1$ is:

—$(CH_2)_n$— or

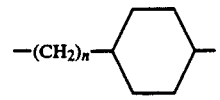

or

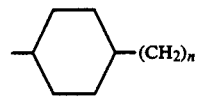

where $n = 1$ to $10$; and where $R_2$ is selected from the group consisting of o- and p-nitrophenyl, 2-chloro-4-nitrophenyl, cyanomethyl, 2-mercaptopyridy, hydroxybenztriazole, N-hydroxysuccinimide, trichlorophenyl, tetrafluorophenyl, 2-fluorophenyl, 4-fluorophenyl, 2,4-difluorophenyl, o-nitro-p-sulfophenyl, N-hydroxyphthalimide, N,N-diethylamino, N-hydroxypyrrolidone, tetrafluorothiophenyl, and 2,3,5,6-tetrafluorophenyl. The preferred heterobifunctional reagent is succinimidyl 4-(N-maleimidomethyl)cyclohexane-1-carboxylate (SMCC) or derivatives thereof.

The reaction is conducted under reactive conditions, thereby forming a derivatized protein. The derivatized protein is separated from the reaction mixture and combined in a preselected molar ratio with an antibody or antibody fragments under reactive conditions, such that at least one native disulfide bond of the antibody or antibody fragments is reduced to produce at least one thiol group capable of forming a thioether bond between said thiol group and the maleimide group of the derivatized toxin, thereby forming an immunoconjugate.

Any biological protein containing native disulfide groups may be employed in the present invention by reduction of same to thiol groups by the utilization of DTT or other reagents capable of forming thiol groups.

Preferred proteins are selected from the group consisting of holotoxins, carrier proteins for drugs, biological response modifiers, chelating proteins, and chelating peptides. Preferred toxins include ricin, abrin, diphtheria toxin, and *Pseudomonas* exotoxin A. Carrier proteins for drugs may be employed in the present invention. For example, human serum albumin (HSA) conjugated with a drug be used. As used herein, the term "drug" shall mean any pharmacologically active entity. Alternatively employed may be proteins or organic molecules capable of biologic response modification or chelates of diagnostic (gamma emitting), therapeutic (alpha or beta emitting) and Auger electron isotopes.

Preferred antibodies are monoclonal antibodies, especially those selected from the group consisting of anti-TAC, or other interleukin 2 receptor antibodies; 9.2.27 and NR-ML-05 to human melanoma-associated proteoglycan; NR-LU-10 to 37–40 kilodalton pancarcinoma glycoprotein, and OVB3 to an as yet unidentified antigen. Polyclonal antibodies may also be employed in the present invention, as well as antibody fragments including F(ab')2 and F(ab'), and genetically engineered antibodies or fragments with an available sulfhydryl.

In the preferred methodology, the preselected molar ratio for conjugation can range from approximately 0.5:1 to approximately 5:1. However, it is preferred that equimolar ratios of toxin and antibody are offered. Due to the favorable reaction conditions and the unexpected nature of the heterobifunctional linking groups described above, yields of 1:1 (protein:antibody) conjugate can range from approximately 53% to approximately 100% of offered antibody or toxin.

An alternative embodiment of the present invention includes immunoconjugates produced according to the foregoing methodology.

An additional aspect of the present invention includes a method for increasing target localization of immunoconjugates of the present invention to a tumor or a target cell or tissue comprising the step of administering an effective dose of the thioether-linked immunoconjugate that is pharmacologically tolerated.

Other aspects of the invention will become evident upon reference to the following detailed description and attached figures.

BRIEF DESCRIPTION OF THE DRAWINGS

FIG. 1 depicts a representative fast protein liquid chromatography (FPLC) gel filtration profile of a disulfide-linked PE:anti-TAC conjugate. Peak "a" represents disulfide-linked conjugate species that correspond to molar ratios of PE:MAb of 3:1 and higher. Peak "b" corresponds to 1:1 conjugate ratios; peak "c" corresponds to unconjugated antibody; and peak "d" corresponds to unconjugated toxin.

FIG. 2 illustrates a representative FPLC gel filtration profile of a thioether-linked PE:NR-LU-10 conjugate. Peaks "a, b, c, and d" correspond to respective peaks in FIG. 1. An unexpectedly high yield of 1:1 conjugate was found.

FIG. 3 depicts FPLC profiles of PE:9.2.27 conjugates linked by a variety of thioether bonds using different heterobifunctional reagents after 30 minutes of conjugation. A=SMCC; B=SMPB; and C=MBS. The larger peak of each profile represents a mixture of 1:1 antibody toxin conjugate and MAb, which are not resolved, while the smaller peak represents unconjugated toxin. Conjugation efficiency can be estimated by the reduction in the unconjugated toxin peak.

FIG. 4 depicts FLPC gel filtration profiles of PE:OVB3 immunoconjugates. A=SMCC; B=SMPB; C=MBS; and D=a unconjugated mixture of OVB3 and PE.

FIG. 8 compares blood clearance of PE:9.2.27 conjugates in a nude mouse xenograft model of human melanoma. +, thioether; □, disulfide.

FIG. 9 compares tumor localization and biodistribution of $125_{I-PE:9.2.27}$ conjugates in a nude mouse xenograft model of human melanoma\\\\,thioether; ////, disulfide.

BEST MODE FOR CARRYING OUT THE INVENTION

Figure 5:
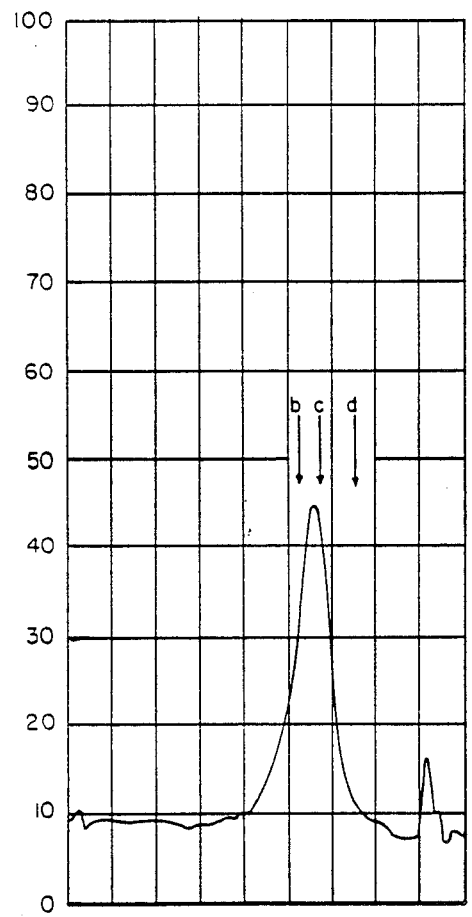
FIG. 5 depicts an FPLC gel filtration profile of human serum albumin (HSA) and NR-ML-05, a monoclonal antibody specific to a 250-kilodalton melanoma proteoglycan surface antigen. SMCC was utilized in the conjugation according to the principles of the present invention. Peak b=1:1 conjugate, peak c=unconjugated antibody, peak d=unconjugated HSA.

As noted above, the present invention discloses a method for producing an immunoconjugate joined by thioether bonds. One advantage of this method is that conjugates may be formed by reacting native thiol groups of an intact antibody molecule or fragment thereof with a maleimide group of a derivatized toxin, forming a thioether bond. Although early studies on the formation of immunoconjugates utilized native antibody thiol groups, more recent studies feature derivatization of antibodies or antibody fragments with heterobifunctional reagents prior to reaction with derivatized toxin molecules. The change in emphasis was due to the inefficiency in conjugation and the heterogenous nature of conjugate species. Use of reduced native disulfide bonds in antibody together with SMCC derivatized toxin in the current invention gave an unexpected high yield of 1:1 conjugate as well as rapid kinetics for thioether bonds.

Others have suggested that use of native antibody thiol groups leads to overderivatization of the antibody with toxin, with a resultant decrease in yield and potency due to poor control over the generation of the number of sulfhydryl groups. Efforts to avoid overderivatization through the use of derivatized antibody with derivatized toxin typically report yields of 1:1 conjugate in the range of 3% to 30% with offerings of 10:1 (Toxin:AB). The present method allows effective conjugation with toxin: antibody ratios smaller (~1:1) than commonly used in the literature.

Another advantage of the method disclosed is the rapid reaction time for production of immunoconjugates. Many of the reports in the literature perform the conjugation reactions for 16 to 20 hours or overnight. In contrast, the reaction time required for the method of the present invention is 15 minutes or less. Rapid kinetics will allow for better control of the conjugation and a reduced risk of denaturing the reactants.

Yet another advantage of the present invention is a demonstration of the feasibility of in vivo administration of the thioether-linked immunoconjugates. Most prior art references present in vitro data regarding potency and selectivity of immunoconjugates. Several references have indicated that thioether-linked immunoconjugates are less potent for target cells than conjugates joined with a cleavable linker. The present method produces thioether-linked conjugates that are as potent in in vitro cytotoxicity assays as cleavable conjugates. In addition, the present invention provides evidence of reduced toxicity in animals, longer serum half life and increased tumor localization of thioether-linked versus disulfide-linked conjugates.

The method of the present invention utilizes a derivatized toxin formed by reaction of an intact toxin with a heterobifunctional reagent. Preferred toxins include intact or holotoxins (containing an A chain and B chain). A particularly preferred toxin is intact *Pseudomonas* exotoxin A.

Heterobifunctional groups to be employed in the present invention have the following general formula:

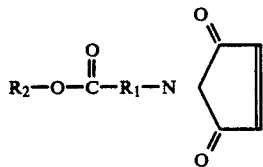

where $R_1$ is:

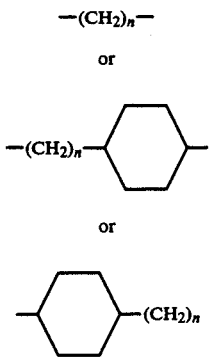

where n=1 to 10; and
where $R_2$ is selected from the group consisting of o- and p-nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, 2-fluorophenyl, 4-fluorophenyl, 2,4-difluorophenyl, o-nitro-p-sulfophenyl, N-hydroxyphthalimide, N,N-diethylamino, N-hydroxypyrrolidone, tetrafluorothiophenyl, and 2,3,5,6-tetrafluorophenyl. The preferred heterobifunctional reagent is succinimidyl 4-(N-maleimidomethyl)cyclohexane-1-carboxylate (SMCC) and derivatives thereof.

It will be evident to one skilled in the art that other heterobifunctional reagents with functionally equivalent reactive end groups may also be employed within the present invention. However, the data show that maleimido-benzoyl-N-hydroxy-succinimide ester (MBS) and succinimidyl 4-(maleimidophenyl)butyrate (SMPB) are excluded from the preferred group of linkers.

The $R_2$ moiety is the leaVing portion of an ester group commonly referred to as an "active ester." The term "active ester" is known to refer to esters which are highly reactive in nucleophilic substitution reactions. Preferred active esters for use in the present invention are highly reactive toward polypeptides or proteins containing lysine residues having epsilon amino groups. The leaving groups of the active esters are sufficiently electron-withdrawing to increase the susceptibility to attack of the carbonyl of the ester by nucleophilic groups on the protein. Typically, an amide bond is thus formed with the aforementioned lysine groups.

The derivatized toxin is then combined with reduced antibody or antibody fragments under conditions permitting the reaction of at least one native antibody thiol group with a maleimide group of the derivatized toxin. Monoclonal and polyclonal antibodies, F(ab')2 fragments, F(ab') fragments as well as engineered antibody fragments may be employed, with monoclonal antibodies and their fragments being particularly preferred. In a preferred embodiment, monoclonal antibodies directed against the IL-2 receptor a human melanoma-associated glycoprotein/proteoglycan or a 37-41 kd pan-carcinoma glycoprotein are utilized. Particularly preferred are monoclonal antibodies anti-TAC and 9.2.27, NR-ML-05, NR-LU-10, and $OVB_3$.

To summarize the examples which follow, Example I describes the preparation of disulfide-linked and thioether-linked immunoconjugates utilizing the MAbs anti-TAC and NR-LU-10 and *Pseudomonas* exotoxin. Example II provides a comparison of the various heterobifunctional reagents and their relative efficiency in producing immunoconjugates. Example III provides the details of minimal derivatization of the antibody by reduction of its native disulfide bonds using DTT. Example IV provides data comparing the in vitro toxicity of disulfide- and thioether-linked conjugates. Example V discloses the differences between the biodistribution and toxicology of thioether and disulfide-linked conjugates. Example VI provides an immunoconjugate utilizing human serum albumin (HSA) as a carrier for drugs.

The following examples are offered by way of illustration and not by way of limitation.

EXAMPLES

Example I

Preparation of Disulfide-Linked and Thioether-Linked Immunoconjugates

In an initial study, cleavable and noncleavable linkages of toxin and antibody were utilized to form immunoconjugates, and the resultant products were compared. Two monoclonal antibodies were employed within this example. The first, anti-TAC, is directed against the IL-2 receptor (T. Uchiyama et al., *J. Immunol.* 126:1393, 1981); the second, NR-LU-10, recognizes a 40 kd glycoprotein, (T. Okobe et al., *Cancer Res.* 44:5273, 1984). Anti-TAC MAb was used to form disulfide-linked conjugates; NR-LU-10 was used to form thioether-linked conjugates.

Disulfide-bonded (cleavable) immunoconjugates were produced by a modification of the method of R. Pirker et al., *J. Clin. Invest.* 76:1261, 1985. Briefly, both monoclonal antibody and *Pseudomonas* exotoxin A (PE) were reacted with 2-iminothiolane in a molar ratio of 1:5 (protein:linker). Unreacted molecules were removed by gel filtration, and then derivatized anti-TAC was reacted with dithiobis(2-nitrobenzoic acid) (DTNB). Excess DTNB was removed, and the DTNB-anti-TAC was reacted with derivatized PE at room temperature for up to 4 hours.

PE was conjugated to NR-LU-10 through a thioether linkage. The PE was first reacted with succinimidyl 4-(N-maleimidomethyl)cyclohexane-1-carboxylate (SMCC) at a molar ratio of 1:10 (protein:linker). Excess heterobifunctional reagent was removed from derivatized PE by gel filtration. NR-LU-10 was treated with 25 mM dithiothreitol (DTT) in 0.01 M phosphate-buffered saline, pH 7.5 (PBS), and excess DTT was removed by gel filtration. The derivatized toxin and the reduced antibody components were mixed and incubated at room temperature for 15+ minutes.

The conjugation reaction mixtures were then fractionated by FPLC gel filtration on a TSK 3000 column at 0.5 ml/min to separate conjugate from unconjugated antibody and unreacted derivatized PE. FIG. 1 shows that the disulfide-linked conjugate species were distributed over a broad range of sizes, which corresponded to molar ratios of PE:MAb of 3:1 and higher, 2:1 and 1:1. The preferred species of conjugate is the 1:1 PE:MAb ratio, because reagents are utilized most economically and biological activity of the antibody portion of the conjugate is optimal. Disulfide conjugation provided a 1:1 PE:MAb conjugate yield of 30%, with an offering ratio of 3:1 PE:MAb. FIG. 2 demonstrates that the SMCC (thioether)linked conjugation mixture fractionated into a single size range, which primarily corresponded to a 1:1 molar ratio of PE:MAb. The yield of 1:1 conjugate was approximately 80%, with an offering ratio of 1:1 PE:MAb. The data indicate that formation of thioether linkage of toxin and antibody is significantly more efficient than formation of disulfide linkage for production of the desired 1:1 toxin:antibody conjugate species.

Example II
Analysis of Heterobifunctional Reagents to Determine Optimal Thioether Conjugation A variety of bifunctional cross-linking reagents contain an active ester group and a maleimide group useful in forming thioether conjugates of PE and MAb 9.2.27. The family of reagents are then examined by FPLC chromatography to determine the most efficient thioether-linking reagent.

Each heterobifunctional reagent was first reacted with PE (1:10 ratio of PE:reagent) at pH 8.5 at room temperature, resulting in derivatization of approximately 1-3 lysine groups of PE. Monoclonal antibody 9.2.27 was reduced with 25mM DTT, pH 7.5, at room temperature, producing free —SH groups. The derivatized toxin and reduced MAb were each separated from unreacted components prior to mixing, and conjugation was conducted at room temperature for 15 minutes. The resultant conjugation mixture was analyzed for the presence of free toxin, free antibody, and conjugate by FPLC gel filtration.

FIG. 3 shows the results obtained with FPLC analysis utilizing MAb 9.2.27 (Morgan et al., *Hybridoma* 1:27, 1981). FIG. 4 shows similar results utilizing Mab OVB$_3$ (Willingham, Fitzgerald, and Pastan, *Proc. Natl. Acad. Sci., USA* 84:2474,1987). Conjugation of toxin to antibody results in: (i) a slight shift in the retention time of the antibody peak (compare profiles A and E); (ii) a broadening of the antibody peak, representing the presence of both 1:1 conjugate and antibody within the peak; and (iii) a reduction in the amount of free toxin present. FIG. 4 shows similar results. Because 1:1 conjugate and unconjugated antibody are not well resolved, the reduction of the unconjugated toxin peak is the best representation of efficient conjugation. FPLC analysis demonstrated that SMCC was the most efficient conjugating reagent, as indicated by the minimal peak of free toxin remaining after conjugation. In decreasing order of linker efficiency, SMCC was followed by SMPB. MBS was the least efficient thioether heterobifunctional reagent. The MBS conjugation mixture was characterized by an FPLC profile essentially identical to that produced by an unconjugated mixture of toxin and MAb.

Example III
Titration of DTT Reduction of MAb For Optimal Conjugation with SMCC and SMPB Optimization of the efficiency of thioether-linking heterobifunctional reagents is also a function of the extent of MAb reduction. In principle, the most efficient conjugation would utilize the least derivatized toxin with the most minimally reduced antibody, thereby providing fewer free sulfhydryl groups for reaction with derivatized toxin.

MAb NR-ML-05 (to the same antigen as 9.2.27) was reacted with 25, 15, 10 or 5 mM DTT prior to conjugation with either SMCC-PE or SMPB-PE. The data showed that SMCC-pE reacted with similar efficiency with MAb reduced with 25, 15, 10, or 5 mM DTT. In contrast, SMPB-PE demonstrated decreasing conjugation yields with MAb exposed to decreasing concentration of DTT.

The efficiency of SMCC-pE was further analyzed by examining DTT concentrations of 25, 10, 5, 1, 0.1, 0.01 mM for reduction of MAb OVB3. The data demonstrated that SMCC-PE produces appreciable amounts of conjugate at DTT concentrations as low as 1 mM, with an optimum at 10mM. Some heterobifunctional linkers (e.g., SMPB and MBS, did not demonstrate appreciable conjugation below concentrations of 10 mM DTT.

Figure 6:
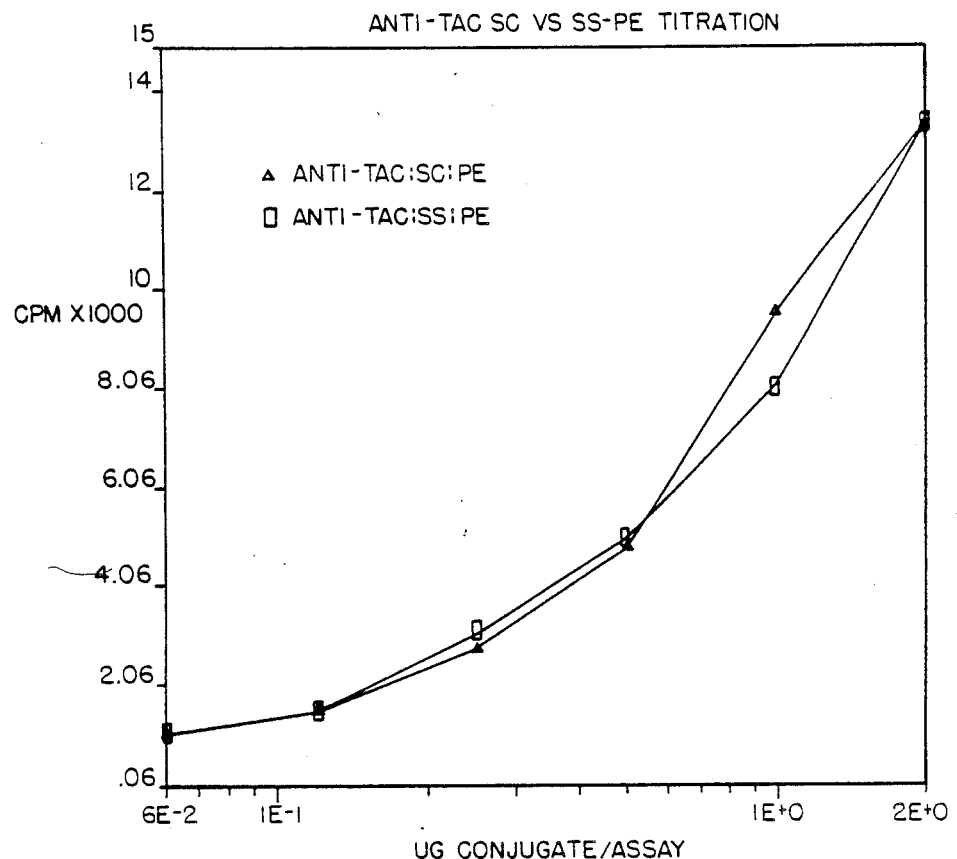
FIG. 6 compares ADP-ribosylating activity of PE:anti-TAC conjugates linked by disulfide or thioether bonds. Δ, thioether; □, disulfide.
Figure 7:
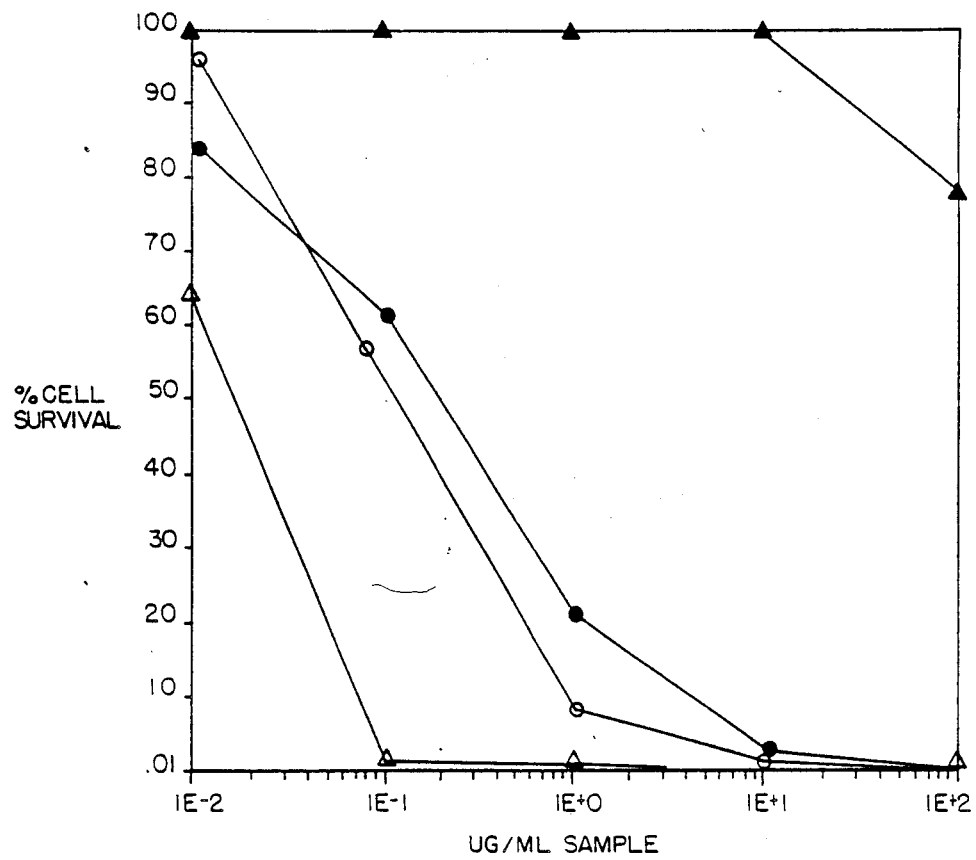
FIG. 7 compares potency and selectivity of PE:anti-TAC and unconjugated PE versus antigen positive (HUT 102) and antigen negative (CEM) cells. Δ, PE:anti-TAC vs. HUT102; ▲, PE:anti-TAC vs. CEM; ●, PE vs. HUT102; ○, PE vs. CEM.

Example IV
In Vitro Cytotoxicity of Disulfide- and Thioether-Linked Conjugates ADP-ribosylation by disulfide- and thioether-linked conjugates was compared in a cell-free system (B.G. Vanness et al., *J. Biol. Chem.* 255:10717, 1980). Prior to titration of ADP-ribosylating activity, the conjugates were treated with 8 M urea and 1 M DTT. In this cell-free system, PE alone is maximally active in the presence of reducing and denaturing agents. As depicted in FIG. 6, disulfide- and thioether-linked 1:1 PE:anti-TAC conjugates are equally potent cytotoxins. Equivalent cytotoxicity is observed despite the fact that the thioether-linked conjugates would not be expected to be cleaved under the conditions of the assay.

In vitro cytotoxicity testing was performed according to the method of A.C. Morgan, Jr. et al., JNCI, 78:1101 (1987), using $^3$H-leucine incorporation to measure protein synthesis inhibition. For testing of PE:9.2.27 conjugates, two human melanoma cell lines were utilized as targets–A375 met mix (antigen-positive) and A375 1° (antigen-negative). For assay of PE:anti-TAC conjugates, target cells were HUT 102 (antigen-positive) and CEM (antigen-negative) (D. J. P. Fitzgerald et al., *J. Clin. Invest.* 74:966, 1984). Conjugates were examined in two formats: (a) short exposure, wherein the conjugate was incubated with target cells for one hour at 37° C., the monolayer gently washed, and the cultures continued for up to 72 hours before the addition of $^3$H-leucine; and (b) long exposure, wherein the conjugate was added and the target cells exposed for the entire length of the culture period.

Thioether- and disulfide-linked conjugates of PE:anti-TAC were equipotent in the in vitro cytotoxicity assay, but selectivity was improved with the non-cleavable linker. The corresponding data obtained with PE:9.2.27 conjugates are presented in Table 1.

TABLE 1

| In Vitro Cytotoxicity of Thioether- and Disulfide-Linked PE:9.2.27 Conjugates | | |
|---|---|---|
| | ID$_{50}$* | |
| | S-C | S-S |
| Antigen-Positive Cell Line | $4 \times 0^{-11}$ | $8 \times 10^{-11}$ |

TABLE 1-continued

In Vitro Cytotoxicity of Thioether- and
Disulfide-Linked PE:9.2.27 Conjugates

| | ID$_{50}$* | |
|---|---|---|
| | S-C | S-S |
| Antigen-Negative Cell Line | $2 \times 10^{-8}$ | $4 \times 10^{-10}$ |

Moles of PE:9.2.27 conjugate, 1:1
S-C, thioether-bonded; S-S, disulfide-bonded.
*Inhibition Dosage for 50% efficacy In general, the PE:9.2.27 conjugates were less potent than the PE:anti-TAC conjugates, but the disulfide and thioether-linked PE:9.2.27 conjugates were equipotent when compared to each other. Disulfide conjugates of intact antibody and toxin were more selective than conjugates of F(ab') and toxin. Thioether linkage improved the selectivity of both intact antibody:toxin and F(ab'):toxin conjugates, as compared to the disulfide-linked analogs.

Example V

Biodistribution and Toxicology of Thioether- and Disulfide-Linked Conjugates Tumor localization and biodistribution of conjugates were examined in a nude mouse xenograft model of human melanoma, according to the method of K. M. Hwang et al., *Canc. Res.* 450:4150, 1985. PE was radiolabeled with 125I-para-iodophenyl (PIP) (D. S. Wilbur et al., *J. Nucl. Med.* 27:959, 1986). This radiolabel is not subject to dehalogenation, and thereby can be used to more effectively follow the biodistribution of conjugates. Animals were sacrificed at 20 hours post-injection, and organs were blotted, weighed and counted. A %dose per gram was calculated for each tissue. In addition, serum half-life was estimated by retroorbital sampling of whole blood.

Mice were administered different doses of PE:anti-TAC and PE:9.2.27 conjugates intraperitoneally. Disulfide-linked conjugates exhibited an LD100 of 1 to 5 ug per mouse; thioether-linked conjugates displayed significantly less toxicity (LD100 of 7.5 to 10 ug per mouse). The serum half-life of PE:9.2.27 thioether conjugates was 3 hours, as compared to disulfide-linked PE:9.2.27, which had a serum half-life of 90 minutes (FIG. 8). The resultant tumor localization and biodistribution of PE:9.2.27 disulfide and thioether conjugates are shown in FIG. 9. If the differences in the blood level between the two linkages are taken into account, the thioether- and disulfide-linked conjugates showed no significant differences in tumor localization and biodistribution, with the exception of kidney and intestine, which displayed higher levels of disulfide-linked conjugates than thioether-linked conjugates.

Nonspecific toxicity of PE:anti-TAC conjugates was also assessed in cynomolgus monkeys. Monkeys were monitored for liver enzyme levels, and were observed for other relevant symptoms, including appetite, presence/absence of nausea, and temperature. Data from this laboratory suggested that nonspecific toxicity of conjugates in monkeys was due to cytolytic effects on liver hepatocytes. Accordingly, the liver enzymes examined in this assay are associated with hepatic function in monkeys. The results are presented in Table 2.

TABLE 2

Peak Liver Function Tests in Cynomolgus
Monkeys Receiving PE:anti-TAC Conjugates

| | | SGOT | SGPT | ALK PHOS. | LDH |
|---|---|---|---|---|---|
| PE:anti-TAC (S-S) | (1 mg)$^x$ | 1310 | 1955 | N.D. | 4259 |
| | (2 mg)* | >5000 | 2500 | N.D. | >6000 |
| PE:anti-TAC (S-C) | (3 mg)· | 69 | 59 | Normal | 700 |

$^x$Vomiting, diarrhea, not eating.
*Animals died.
·Animals received 1 mg, and then an additional 2 mg at day 4.

As shown in Table 2, LDH levels significantly increased with administration of only 1 mg of disulfide-linked PE:anti-TAC. Other liver markers, such as SGOT and SGPT, were also elevated. The monkeys that received the disulfide-linked conjugate also displayed a loss of appetite, nausea and diarrhea at a dose of 1 mg. In contrast, administration of up to 3 mg of thioether-linked PE:anti-TAC produced only slight elevation of LDH levels, and little or no change in SGOT and SGPT levels. In addition, these monkeys exhibited no adverse symptomology. These data indicate that the thioether conjugates of the present invention may be administered to primates and lower mammals at higher doses than disulfide conjugates. The data suggest that nonspecific toxicity of conjugates is significantly decreased when a nonreducible linker is used for conjugation.

Example VI

Conjugation of Antibody to a Non-Toxin Moiety

The conjugation efficiency of SMCC has also been demonstrated by conjugation of a monoclonal antibody to a non-toxin protein. MAb NR-ML-05 was reduced with 25 mM DTT and reacted with human serum albumin (HSA) derivatized with SMCC according to the protocol in Example I. FIG. 5 shows that SMCC is as efficient in the conjugation of MAb and HSA as it is for MAb and toxin. HSA has been utilized for conjugation of drugs to antibody (Garnett, M.D., et al., *Int. J. Cancer* 31:661, 1983).

The foregoing examples are illustrative of variants of the present invention. They are not intended to be exhaustive. Other embodiments within the skill of the art are intended to be subsumed within the scope of the invention. For example, efficient thioether conjugation of proteins other than antibodies and toxins are within the scope of the invention, so long as the protein to be linked to the maleimide group has at least one native disulfide bond capable of reduction to a free thiol group and the other protein has lysine residues capable of amide formation with the active ester of the preferred linkers.

I claim:

1. A method for producing a 1:1 protein:anitbody tioether-linked immunoconjugate as a predominant species, comprising the steps of:

combining a protein selected from the group consisting of toxin, carrier protein, biological response modifier, chelating protein or chelating peptide, with a heterobifunctional reagent having the following general formula:

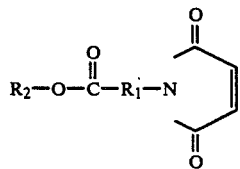

wherein $R_1$ is:

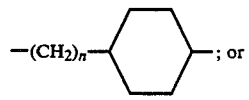

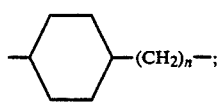

wherein n=1 to 10; and wherein $R_2$ is selected from the group consisting of o- and p-nitrophenyl, 2-chloro-4-nitrophenyl, cyanomethyl, 2-mercaptopyridyl, hydroxybenztriazole, N-hydroxysuccinimide, trichlorophenyl, 2-fluorophenyl, 4-fluorophenyl, 2,4-difluorophenyl, 2,3,5,6,-tetrafluorophenyl, tetrafluorothiophenyl, o-nitro-p-sulfophenyl, N-hydroxyphthalimide, N,N-diethylamino, N-hydroxypyroolidone, under conditions that permit reaction of the protein and $R_2$, thereby forming a derivatized protein;

separating the derivatized protein;

reacting an antibody or antibody fragment with a reducing agent, thereby forming a reduced antibody component;

separating the reduced antibody component; and mixing the derivatized protein and the reduced antibody component in a molar ration of approximately 0.5:1 to approximately 5:1 at room temperature for about 5 minutes to about 60 minutes, such that at least one thiol group of the reduced antibody component and at least one maleimide group of the derivatized protein combine to form a thioether bond, thereby producing the 1:1 protein:antibody thioether-linked immunoconjugate as a predominant species.

2. The method of claim 1 wherein the toxin is selected from the group consisting of Pseudomonas exotoxin A, ricin, abrin and diphtheria toxin.

3. The method of claim 1 wherein the heterobifunctional reagent is succinimidyl 4-(N-maleimidomethyl)-cyclohexane-1-carboxylate (SMCC) or derivatives thereof.

4. The method of claim 1 wherein the antibody fragment is F(ab')$_2$ fragment of F(ab') fragment.

5. The method of claim 1 wherein the antibody is genetically engineered antibody or fragments thereof having an available sulfhydryl group.

6. The method of claim 1 wherein the reducing agent is dithiothreitol (DTT).

7. The method of claim 1 wherein the thioether-linked immunoconjugate is formed as a 1:1 protein:antibody conjugate in a yield of about 50% to about 100%.

8. A thioether-linked immunoconjugate produced according to the method of claim 1.

* * * * *

UNITED STATES PATENT AND TRADEMARK OFFICE
CERTIFICATE OF CORRECTION

PATENT NO. : 4,981,979
DATED : January 1, 1991
INVENTOR(S) : Sivam

It is certified that error appears in the above-indentified patent and that said Letters Patent is hereby corrected as shown below:

In column 14, line 60 [claim 1], please change "anitbody" to --antibody-- and "tioether" to --thioether--.

In column 15, line 33 [claim 1], please change "N-hydroxypyroolidone" to --N-hydroxypyrrolidone--.

In column 16, line 7 [claim 1], please change "ration" to --ratio--.

In column 16, line 24 [claim 4], please delete "of" and insert --or-- therefor.

Signed and Sealed this

Thirty-first Day of October 1995

Attest:

BRUCE LEHMAN

Attesting Officer        Commissioner of Patents and Trademarks